(12) United States Patent
Umlauf et al.

(10) Patent No.: US 9,285,374 B2
(45) Date of Patent: Mar. 15, 2016

(54) DIAGNOSTIC METHOD FOR ALZHEIMER'S DISEASE

(75) Inventors: Ellen Umlauf, Vienna (AT); Maria Zellner, Vienna (AT)

(73) Assignee: RANDOX LABORATORIES LIMITED (GB)

( * ) Notice: Subject to any disclaimer, the term of this patent is extended or adjusted under 35 U.S.C. 154(b) by 615 days.

(21) Appl. No.: 13/513,670

(22) PCT Filed: Dec. 3, 2010

(86) PCT No.: PCT/GB2010/052023
§ 371 (c)(1),
(2), (4) Date: Jul. 23, 2012

(87) PCT Pub. No.: WO2011/067610
PCT Pub. Date: Jun. 9, 2011

(65) Prior Publication Data
US 2012/0283127 A1    Nov. 8, 2012

(30) Foreign Application Priority Data

Dec. 4, 2009 (GB) .................................. 0921447.9

(51) Int. Cl.
| | |
|---|---|
| *A61K 39/395* | (2006.01) |
| *G01N 33/68* | (2006.01) |
| *C07K 14/47* | (2006.01) |
| *C07K 14/775* | (2006.01) |
| *C12N 9/06* | (2006.01) |
| *C12N 9/10* | (2006.01) |

(52) U.S. Cl.
CPC ............ *G01N 33/6896* (2013.01); *C07K 14/47* (2013.01); *C07K 14/4716* (2013.01); *C07K 14/775* (2013.01); *C12N 9/0022* (2013.01); *C12N 9/1044* (2013.01); *G01N 2333/775* (2013.01); *G01N 2333/90638* (2013.01); *G01N 2333/91085* (2013.01); *G01N 2800/2821* (2013.01)

(58) Field of Classification Search
None
See application file for complete search history.

(56) References Cited

U.S. PATENT DOCUMENTS

2011/0229917 A1*    9/2011    Krizman et al. ................ 435/15

FOREIGN PATENT DOCUMENTS

| WO | WO 2006/134390 | 12/2006 |
| WO | WO 2011/067610 | 6/2011 |

OTHER PUBLICATIONS

Zellner, et al., "Comparative Platelet Proteome Profiling from Alzheimer's and Parkinson's Disease Patients," Jun. 1, 2009, Clinical Chemistry, American Association for Clinical Chemistry, Washington, DC, pp. A221-A222, XP009144065.
Matsushima, H., et al., "Reduction of Platelet Phospholipase C-Delta1 Activity in Alzheimer's Disease Associated with a Specific Apolipoprotein E Genotype (Epsilon3/Epsilon3)," Jan. 1, 1998, International Journal of Molecular Medicine, Spandidos Publications, GR, pp. 9193, XP009144053.
Li, Y. J., et al., "Revealing the Role of Glutathione S-Transferase Omega in Age-At-Onset of Alzheimer and Parkinson Diseases," Aug. 1, 2006, Neurobiology of Aging, Tarrytown, NY, US, pp. 1087-1093, XP024993158.
Babeluk, R., et al., "Implication of Wild Type Glutathione S-Transferase Omega-1 as a Risk Factor in Non-APOE4 Carriers in Alzheimer's Disease," Jun. 1, 2009, Clinical Chemistry, American Association for Clinical Chemistry, Washington, DC, p. A223, XP009144050.
Marcourakis, Tania, et al., "Apolipoprotein E Genetype is Related to Nitric Oxide Production in Platelets," Dec. 1, 2008, Cell Biochemistry and Function, Butterworth, Guildford, GB, pp. 852858, XP009144052.
Zhao Lingzhi, et al., "Macrophage-Mediated Degradation of Beta-Amyloid Via an Apolipoprotein E Isoform-Dependent Mechanism," Mar. 18, 2009, Journal of Neuroscience, The Society, Washington, DC, US, pp. 3603-3612, XP009144054.
Smith, R. C., et al., "Platelet Monoamine Oxidase in Alzheimer's Disease," Jan. 1, 1982, Journal of Gerontology, C.C. Thomas, Springfield, IL, US, pp. 572-574, XP009076550.
Davies, T.A., et al., "Moderate and Advanced Alzheimer's Patients Exhibit Platelet Activation Differences," Mar. 4, 1997, Neurobiology of Aging, Tarrytown, NY, US, pp. 155-162, XP009144061.
Cattabeni, F., et al., "Platelets Provide Human Tissue to Unravel Pathogenic Mechanisms of Alzheimer Disease," Aug. 1, 2004, Progress in Neuro-Psychopharmacology & Biological Psychiatry, Oxford, GB, pp. 763-770, XP004560938.
Gupta, A., et al., "Coagulation and Inflammatory Markers in Alzheimer's and Vascular Dementia," Jan. 1, 2005, International Journal of Clinical Practice, Medicon International, Esher, GB, pp. 52-57, XP009143967.
International Search Report and Written Opinion issued May 13, 2011, in International Application No. PCT/GB/2010/052023.
International Preliminary Report on Patentability issued Mar. 2, 2012, in International Application No. PCT/GB/2010/052023.
Li, Y., et al., "Glutathione S-transferase omega-1 modifies age-at-onset of Alzheimer disease and Parkinson disease," Human Molecular Genetics, vol. 12, No. 24, pp. 3259-3267, (2003).

* cited by examiner

*Primary Examiner* — Michele K Joike
(74) *Attorney, Agent, or Firm* — Saliwanchik, Lloyd & Eisenschenk

(57) ABSTRACT

The present invention provides an ex vivo method for aiding the diagnosis of Alzheimer's disease in a patient, the method comprising the steps of determining the level of expression of at least four platelet proteins in a platelet sample from the patient selected from monoamine oxidase-B, coagulation factor Xllla, total tropomyosin (a and 13), WD-repeat protein 1 and apolipoprotein E4; and comparing the result of (i) to a control value, wherein a result higher than the control value is indicative of Alzheimer's disease. Preferably, the method of the invention further comprises determining the level of expression of wild-type GSTO-1 or mutant GSTO-1.

13 Claims, 12 Drawing Sheets

DIAGNOSTIC METHOD FOR ALZHEIMER'S DISEASE

CROSS-REFERENCE TO RELATED APPLICATIONS

This application is a national stage application under 35 U.S.C. §371 of International Application No. PCT/GB2010/052023, titled DIAGNOSTIC METHOD FOR ALZHEIMER'S DISEASE, filed Dec. 3, 2010, which claims priority to Great Britain Patent Application No. 0921447.9, filed Dec. 4, 2009, both of which are hereby incorporated by reference in their entireties.

FIELD OF INVENTION

This invention relates to an ex vivo diagnostic method using the quantification of peripheral biomarkers of Alzheimer's disease.

BACKGROUND OF THE INVENTION

Alzheimer's disease is a neurodegenerative disorder, afflicting approximately 24 million people worldwide. The disease is characterised by cognitive and behavioural dysfunction resulting from loss of neurons and synapses in the cerebral cortex and certain sub-cortical regions of the brain.

The disease can begin many years before it is eventually diagnosed. In the early stages, short-term memory loss is the most common symptom. Later, symptoms include confusion, anger, mood swings, language breakdown, long-term memory loss, and the general decline of senses and bodily functions.

Alzheimer's disease is the most common type of dementia in the elderly and affects almost half of all patients with dementia. Correspondingly, advancing age is the primary risk factor for the disease. Among people aged 65, 2-3% show signs of the disease, while 25-50% of people aged 85 have symptoms of Alzheimer's and an even greater number have some of the pathological hallmarks of the disease without the characteristic symptoms. The World Health Organisation estimates that globally the total disability adjusted life years (DALY) for Alzheimer's disease and other dementias exceeded 11 million in 2005, with a projected 3.4% annual increase. There is at present no known cure for Alzheimer's disease, and available treatments offer relatively small symptomatic benefits and are palliative in nature.

Depression is a common early symptom in Alzheimer's disease and is believed to be attributed to, amongst other factors, up-regulation of the enzyme monoamine oxidase (MAO). There are two isoforms of this enzyme, MAO-A and MAO-B. Both are found throughout the cells of the central nervous system (CNS), where they function to inactivate monoaminergic neurotransmitters including phenethylamine and dopamine. MAO-B is also abundant in blood platelets.

The onset and progression of Alzheimer's disease is associated with the development of amyloid plaques and neurofibrillary tangles. Amyloid plaques (also known as "senile plaques") comprise dense insoluble deposits of beta-amyloid, a protein derived from the transmembrane protein amyloid precursor protein (APP). Following the proteolysis of APP, beta-amyloid proteins aggregate extracellularly, forming plaques. Neurofibrillary tangles are formed due to hyper-phosphorylation of tau, a microtubule-associated protein that is abundant in the CNS. Multiple hyperphosphorylated tau molecules become entangled and form masses within nerve cell bodies. Such neurofibrillary tangles cause microtubules to disintegrate, resulting in collapse of the neuronal transport system.

Alzheimer's disease is usually diagnosed clinically from the patient history, observations of relatives, and clinical observations. However, the presence of Alzheimer's disease-characteristic neurological and neuropsychological features such as amyloid plaques and neurofibrillary tangles can often only be determined post-mortem.

Most cases of Alzheimer's disease do not exhibit familial inheritance, however at least 80% of sporadic Alzheimer's cases involve genetic risk factors. Inheritance of the ε4 allele of the apolipoprotein E (ApoE) gene is regarded as a risk factor for development in up to 50% of late-onset sporadic Alzheimer's cases.

Glutathione S-transferase omega-1 (GSTO-1) is a member of the gluthathione S-transferase family of enzymes that catalyse the conjugation of reduced glutathione (GSH) with various hydrophobic substrates bearing electrophilic centres. The gene encoding GSTO-1 is known to exist in different genetic isoforms. These isoforms correlate with the age-at-onset (AAO) of Alzheimer's disease and Parkinson's disease (Li, Y et al., Hum Mol Genet. (2003) 12(24):3259-67). Li and co-workers described that the GSTO-1h SNP 7-1 (rs4825, A nucleotide) is associated with an AAO delay of 6.8 years (+/−4.41) for Alzheimer's disease and 8.6 years (+/−5.71) for Parkinson's disease (Li, Y et al., Neurobiol Aging (2006) 27(8):1087-93).

Diagnostic markers for neurological disorders are especially important in diagnosis early in the course of disease, when therapeutic compounds have the greatest potential effect. However, accurate diagnosis is difficult. Few diagnostic markers for early stage neuronal disorders are available and those that are available rely on the analysis of sample material (e.g. cerebrospinal fluid), which is difficult and painful to obtain.

Therefore, there is a need to identify new diagnostic methods using biomarkers of Alzheimer's disease which are available peripherally from easily obtainable patient samples, thereby aiding simple and accurate diagnosis.

SUMMARY OF THE INVENTION

A first aspect of the present invention provides an ex vivo method for aiding the diagnosis of Alzheimer's disease in a patient, comprising:
  (i) determining the level of expression of at least four platelet proteins in a platelet sample from the patient selected from monoamine oxidase-B, coagulation factor XIIIa, total tropomyosin, WD-repeat protein 1 apolipoprotein E4; and
  (ii) comparing the result of (i) to a control value,
wherein a result higher than the control value is indicative of Alzheimer's disease.

A second aspect of the invention is directed to the use of one or more of the proteins identified in Table 3 or Table 4, to normalise biological variation in the expression level of one or more platelet proteins included in the diagnostic method according to the first aspect of the invention.

A third aspect of the invention provides a solid support comprising one or more ligands of at least four platelet proteins selected from monoamine oxidase-B, coagulation factor XIIIa, total tropomyosin, WD-repeat protein 1 and ApoE4, immobilised thereon.

DETAILED DESCRIPTION OF THE INVENTION

Figure 1:
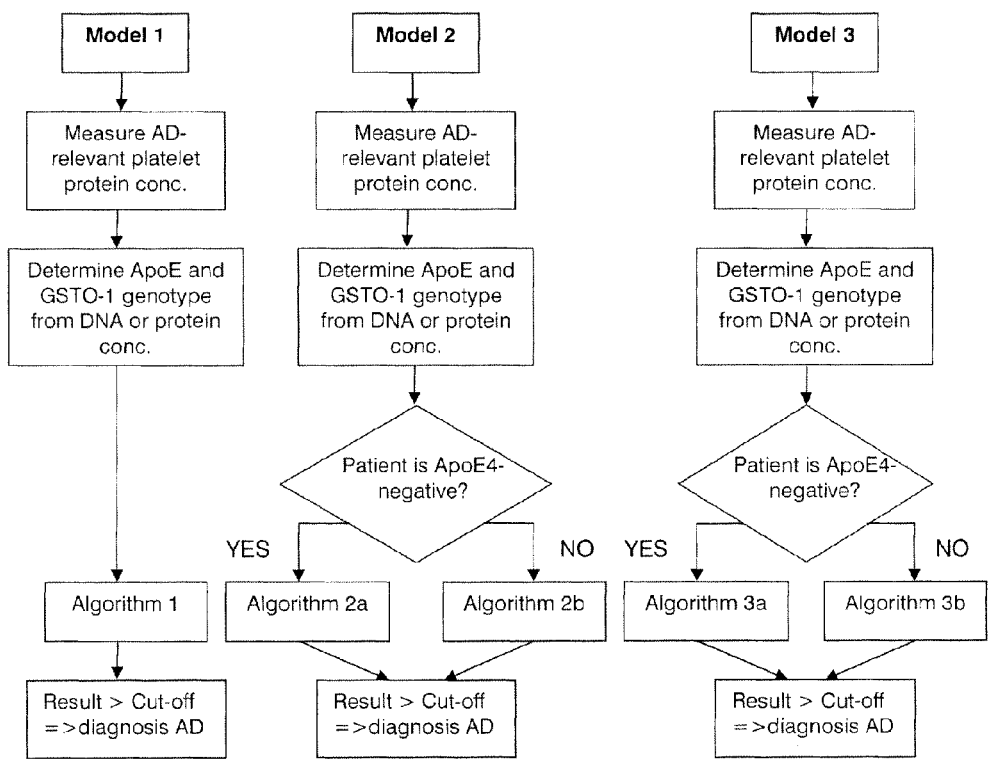
FIG. 1 illustrates the decision process for the use of the respective algorithms of Models 1, 2, 3 and 4.
Figure 1B:
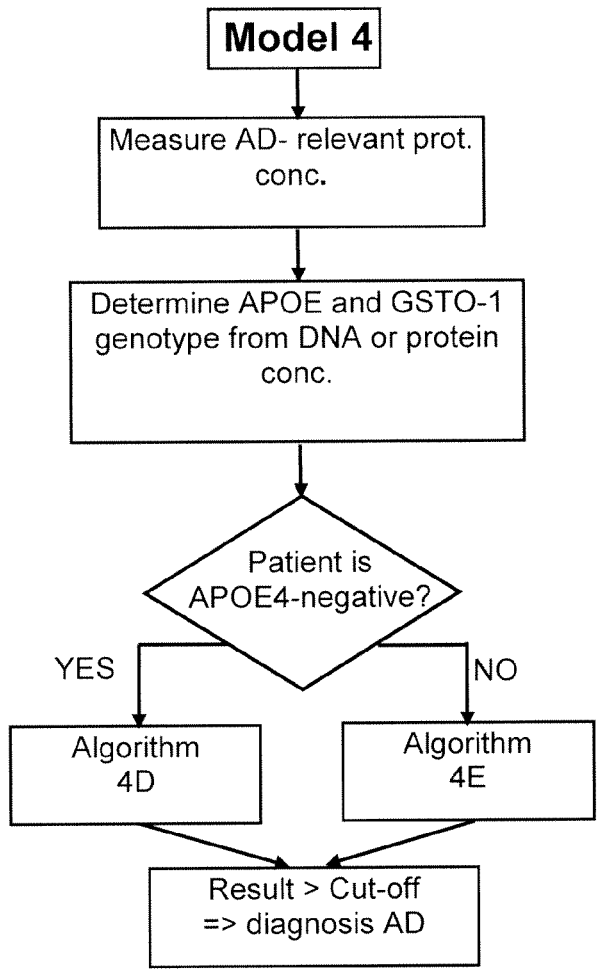
Figure 2A:
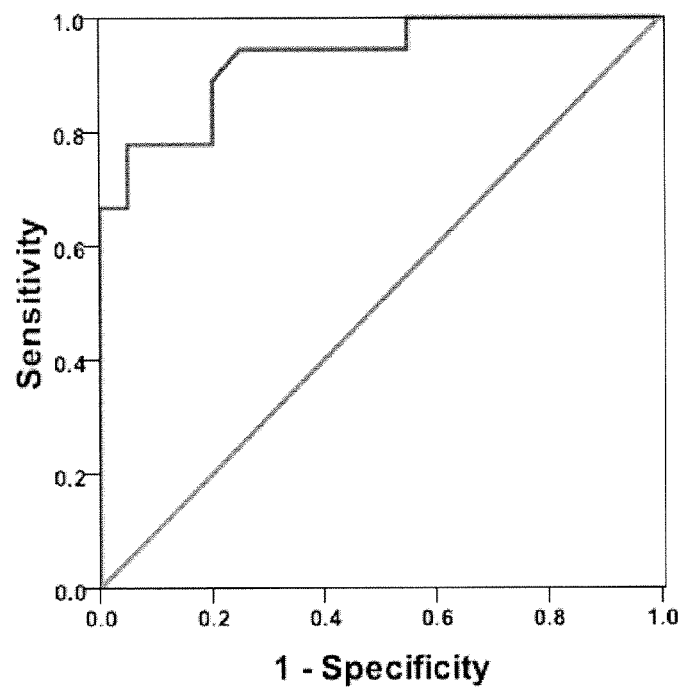
FIGS. 2a and 2b show the ROC curve and scatter plot respectively of the discovery set using Model 1.
Figure 2B:
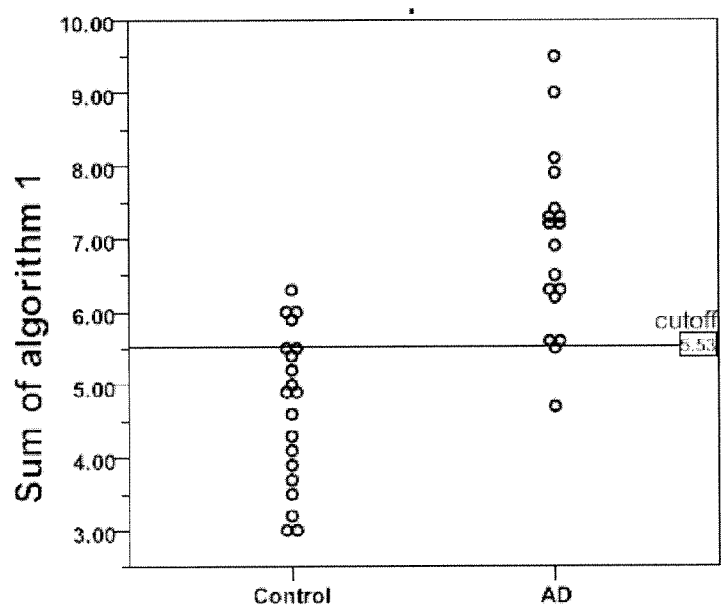
Figure 2C:
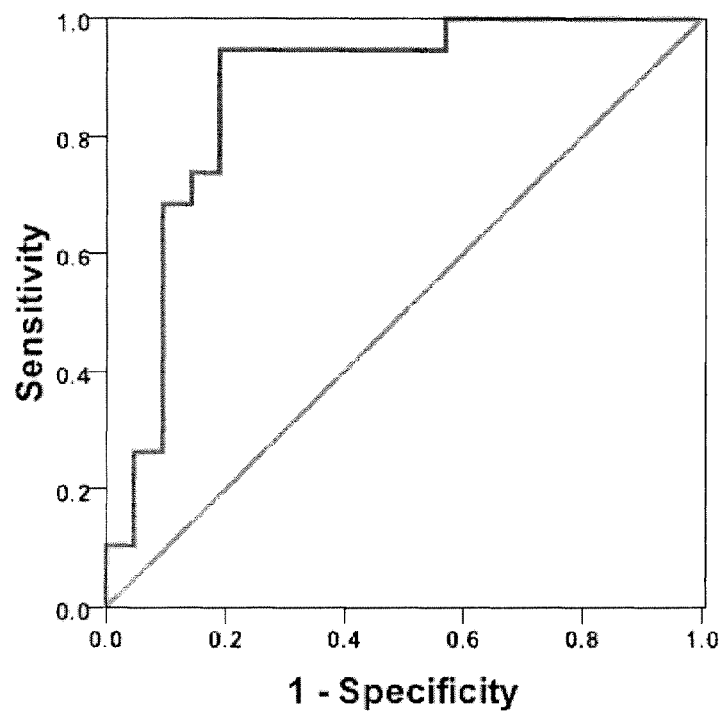
FIGS. 2c and 2d show the ROC curve and scatter plot respectively of the validation set using Model 1.
Figure 2D:
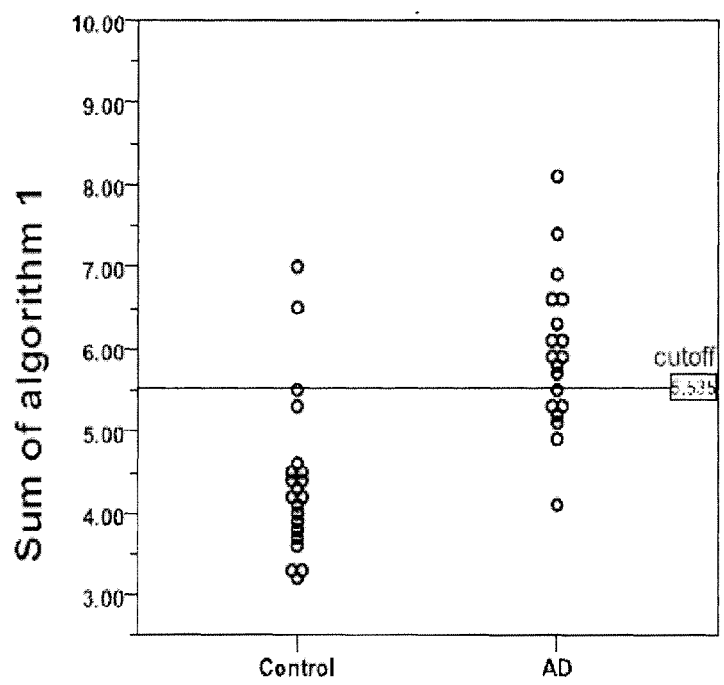
Figure 3A:
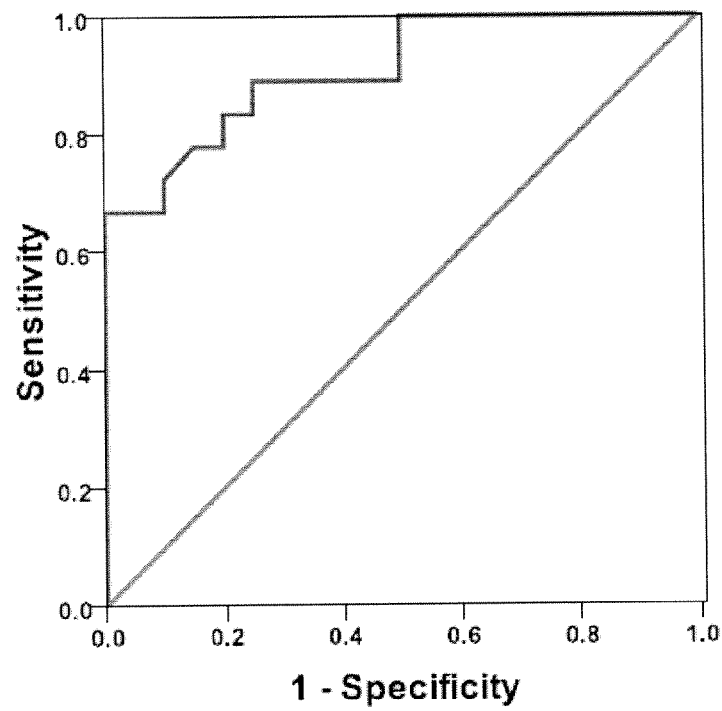
FIGS. 3a and 3b show the ROC curve and scatter plot respectively of the discovery set using Model 2.
Figure 3B:
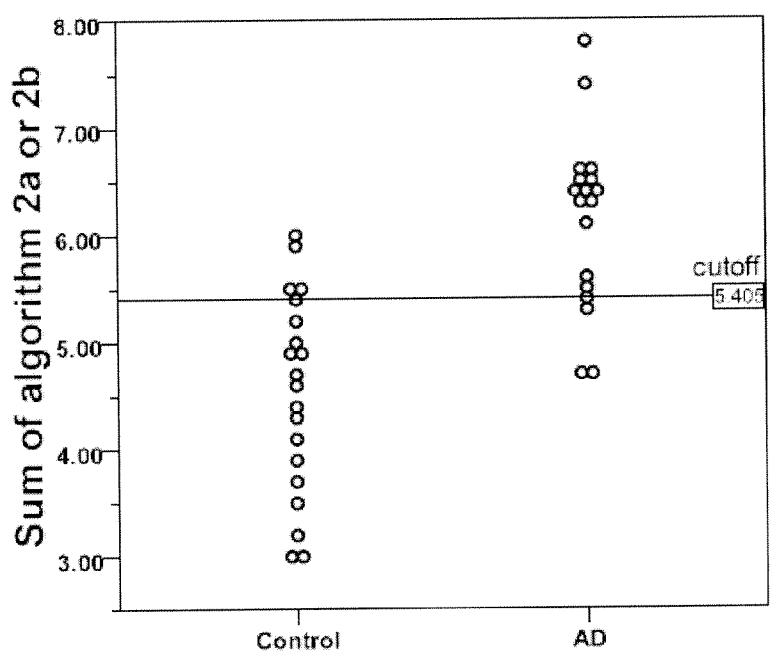
Figure 3C:
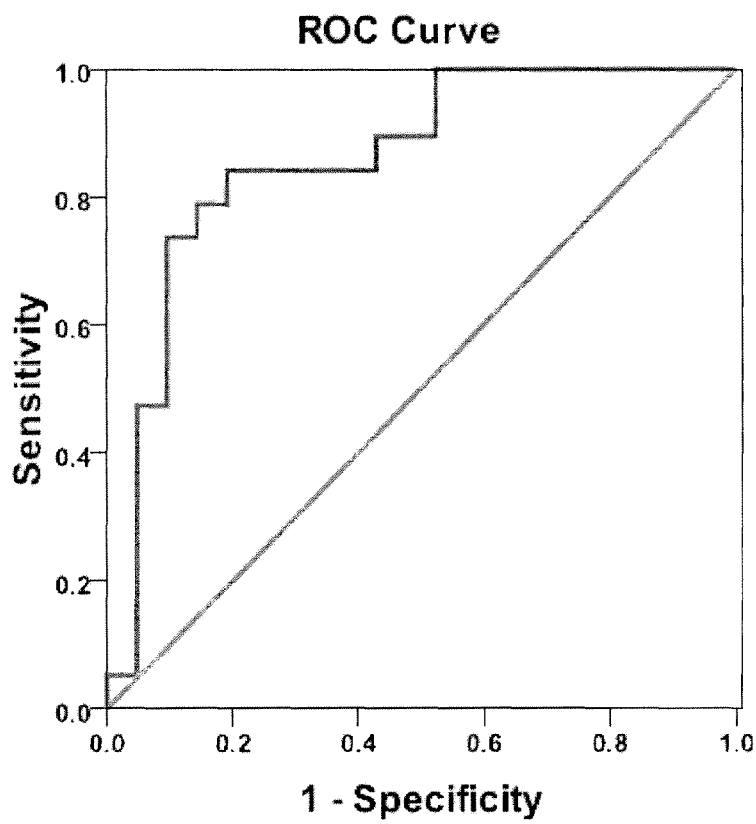
FIGS. 3c and 3d show the ROC curve and scatter plot, respectively, of the validation set using Model 2.
Figure 3D:
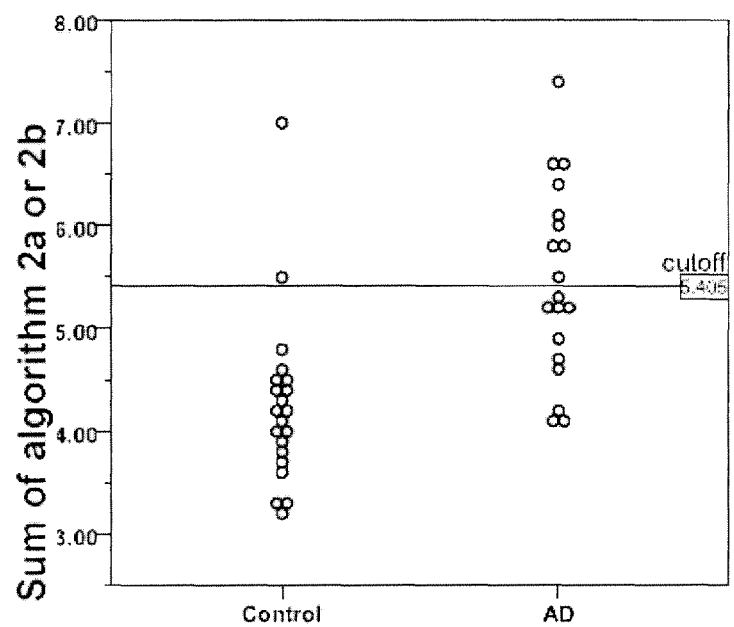
Figure 4A:
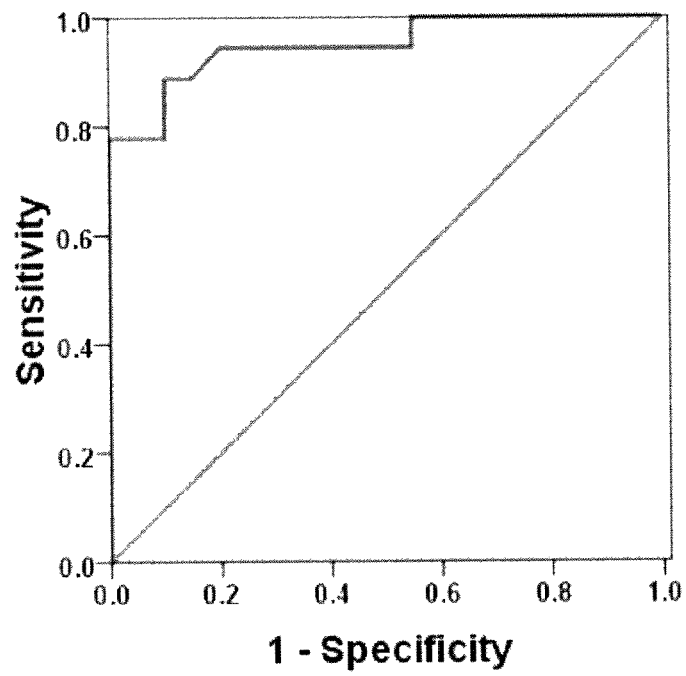
FIGS. 4a and 4b show the ROC curve and scatter plot respectively of the discovery set using Model 3.
Figure 4B:
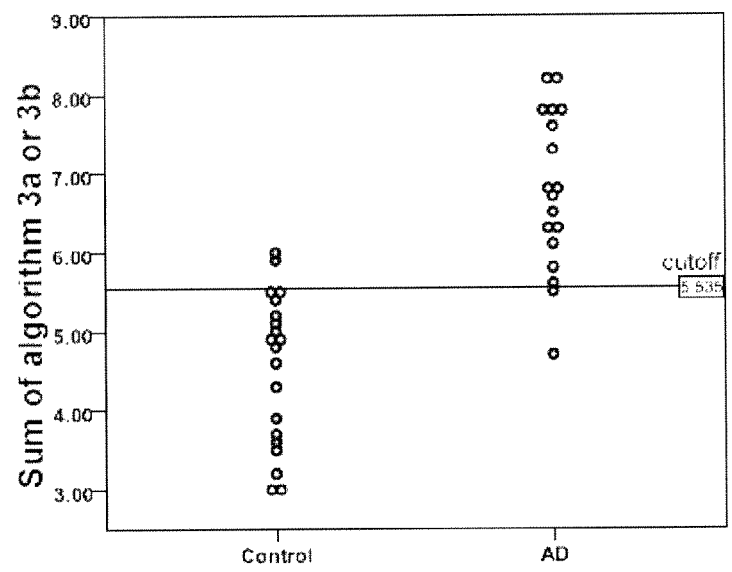
Figure 4C:
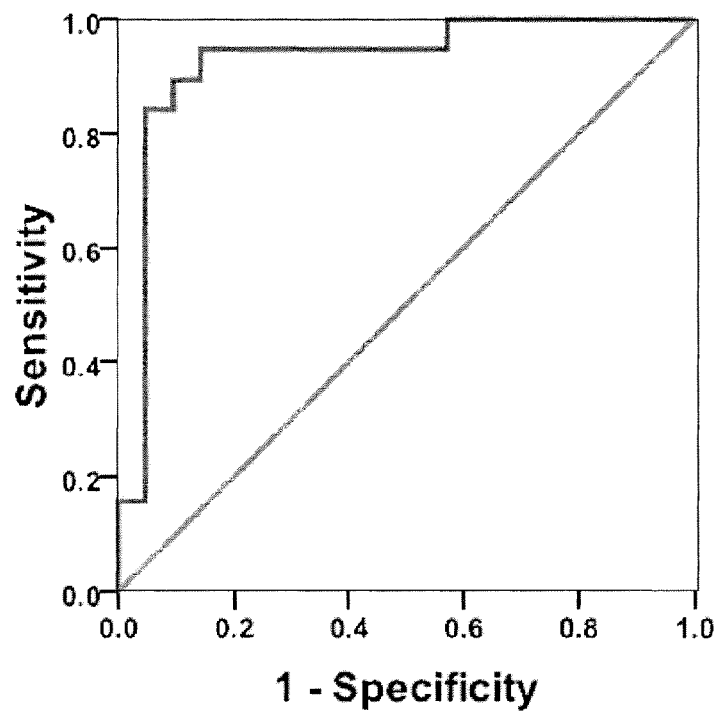
FIGS. 4c and 4d show the ROC curve and scatter plot, respectively, of the validation set using Model 3.
Figure 4D:
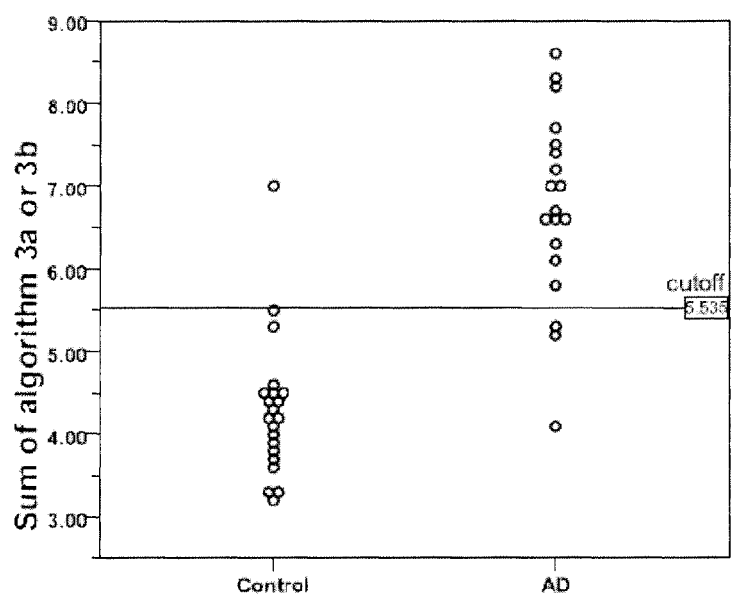

The present invention is based upon the surprising realisation that the expression of the platelet proteins monoamine oxidase-B, coagulation factor XIIIa, α-tropomyosin, β-tropomyosin, WD-repeat protein 1 and apolipoprotein E4 (ApoE4) is significantly changed in Alzheimer's disease patients, compared to age and sex-matched healthy controls. These platelet proteins therefore function as biomarkers of the disease. Furthermore it has been found that wtGSTO-1 (alanine at position 140) is over-represented in Alzheimer's disease patients who do not carry any ApoE4 allele, whereas wtGSTO-1 is under-represented in ApoE4-positive Alzheimer's disease patients.

The present invention provides an ex vivo method for aiding the diagnosis of Alzheimer's disease in a patient, comprising determining the level of expression of at least four platelet proteins in a platelet sample from the patient selected from monoamine oxidase-B, coagulation factor XIIIa, total tropomyosin (α and β), WD-repeat protein 1 and ApoE4 and comparing the combined expression level (measured as standardised abundance) to a control value, wherein a result that is higher than the control value is indicative of Alzheimer's disease. Results higher than the control value may therefore be used to positively diagnose Alzheimer's disease.

The method of the invention can be used to aid the diagnosis of Alzheimer's disease, in conjunction with other methods such as mini-mental state examination (MMSE) score and physician consultation.

As used herein, the term 'patient' refers to a mammal, preferably a human, suspected of having Alzheimer's disease or a person thought to have a predisposition to the disease.

In a preferred embodiment, the sample material is isolated blood platelet lysate, obtained for example by using standard phlebotomy techniques.

The term 'isoform' is defined herein as protein with equivalent function as another protein and a similar or identical sequence but which is encoded by a different gene.

As used herein, the term "gene product" refers to the mRNA or protein product that results from transcription of the gene.

As used herein, the term 'expression level' refers to the amount of the specified protein (or mRNA coding for the protein) in the sampled platelets. Techniques for determining protein expression level will be apparent to the skilled person and include the use of biochip array technology or 2D DIGE (2-dimensional Difference in Gel Electrophoresis).

Preferably, the expression level of specific platelet proteins is quantified in terms of "standardised abundance", which provides a numerical value that takes into account natural variation in the concentration of platelet proteins. The standardised abundance value enables comparison with a known control value.

The term 'peripheral biomarker' is defined as a protein that is present peripherally in blood platelets, wherein alterations in peripheral expression of the protein mirror pathologically significant changes in the CNS, wherein such changes relate to the pathology of Alzheimer's disease.

As used herein, the term 'GSTO-1' refers to the protein identified as EC 2.5.1.18, having the UniProtKB/SwissProt Primary Accession No. P78417 (sequence version 2), or variants and isoforms thereof.

As used herein, the term 'monoamine oxidase' or 'MAO' refers to the protein identified as EC 1.4.3.4, which is an enzyme that catalyses the oxidation of monoamines. In humans there are two forms of MAO, MAO-A which has the UniProtKB/SwissProt Primary Accession No. P21397, and MAO-B which has the UniProtKB/SwissProt Primary Accession No. P27338. Both are present in neurones and astroglia. MAO-A is also present in the liver, gastrointestinal tract and placenta, whereas MAO-B is found in blood platelets.

As used herein, the term "coagulation factor XIIIa" refers to the protein which has the UniProtKB/SwissProt Primary Accession No. P00488 and is encoded in humans by the F13A1 gene. Coagulation factor XIIIa is the catalytically active subunit of coagulation factor XIII and functions in the blood coagulation cascade to stabilise fibrin clots.

Tropomyosin is an actin-binding protein that regulates actin mechanics. Two tropomyosin chains assemble into parallel and in-register coiled-coil dimers. Tropomyosin alpha is encoded by the TPM1 gene in humans and has the UniProtKB/SwissProt Primary Accession No. P09493. Tropomyosin beta is encoded by the TPM2 gene in humans and has the UniProtKB/SwissProt Primary Accession No. P07951. For the purpose of the method of the present invention, the standard abundances of α-tropomyosin and β-tropomyosin are combined to give a value for 'total tropomyosin' which is then used in the assay.

As used herein, the term 'WD-repeat protein 1' refers to the protein having the UniProtKB/SwissProt Primary Accession No. O75083. WD-repeat protein 1 (also known as actin-interacting protein 1) is a highly conserved protein in eukaryotes which functions to induce disassembly of actin filaments in conjunction with ADF/cofilin family proteins.

The term 'ApoE' is an abbreviation of apolipoprotein E. There are three major isoforms of ApoE, known as ApoE2, E3 and E4, encoded by alleles, є2, є3 and є4 respectively. ApoE3 is the most common isoform. ApoE4 is known to be associated with late-onset Alzheimer's disease, with two copies of the є4 allele representing a greater risk of developing the disease than one or no copies of the allele. Alzheimer's patients can therefore be categorised as ApoE4 and non-ApoE4 patients.

As detailed in Table 1, GSTO-1 genotype distribution is dependent upon the ApoE3 and ApoE4 genotype and is significantly changed in non-ApoE4 Alzheimer's and Parkinson's patients. The normal distribution of wild-type (WT) GSTO-1 in the general population has been found to be about 40%, whereas 73% of non-ApoE4 Alzheimer's patients and 71% non-ApoE4 Parkinson's patients have WT GSTO-1. Alzheimer's disease risk can therefore be determined using ApoE4 phenotype or genotype analysis in combination with GSTO-1 phenotype or genotype analysis.

TABLE 1

| Alzheimer's Disease | Parkinson's Disease | Aged Controls | Young Controls |
|---|---|---|---|
| ApoE3 | ApoE3 | ApoE3 | ApoE3 |
| 73% GST (wt) | 71% GST (wt) | 34% GST (wt) | 36% GST (wt) |
| ApoE4 | ApoE4 | ApoE4 | ApoE4 |
| 38% GST (wt) | 0% GST (wt) | 43% GST (wt) | 0% GST (wt) |

Wild-type GSTO-1 is therefore a useful peripheral biomarker of Alzheimer's disease in non-ApoE4 patients, and as shown in Table 1, it enables discrimination between Alzheimer's disease and Parkinson's disease.

The present inventors have found that the use of a combination of at least four biomarkers of Alzheimer's disease provides a more accurate diagnosis than single biomarker assays. Accordingly, the present invention provides an ex vivo method for aiding the diagnosis of Alzheimer's disease comprising the steps of:

(i) determining the level of expression of at least four platelet proteins in a platelet sample from the patient selected from monoamine oxidase-B, coagulation factor XIIIa, total tropomyosin, WD-repeat protein 1 and ApoE4; and (ii) comparing the result of (i) to a control value, wherein a result higher than the control value is indicative of Alzheimer's disease.

In a preferred embodiment, step (i) of the method of the invention further comprises determining the level of expression of either wild-type or mutant GSTO-1. The decision as to which form of GSTO-1 is included in the assay is made with reference to the number of alleles of ApoE4 in the patient's genome. Therefore, a preferred embodiment of the method of the invention further comprises determining the number of alleles of ApoE4. If the patient has one or two alleles, the expression level of mutant GSTO-1 is determined. If the patient has no ApoE4 alleles then the expression level of wild-type GSTO-1 is determined.

In a preferred embodiment, the expression level of each of the platelet proteins is determined with a protein assay that determines the protein level accurately.

In a preferred embodiment, the expression level of each of the platelet proteins is determined using a biochip array. A biochip having ligands for the platelet proteins to be detected immobilised on its surface is contacted with a patient platelet cell lysate sample and the surface of the biochip is then washed, such that proteins present in the sample are identified according to detectable interactions formed with immobilised ligands.

In order for ApoE4 genotyping to be conducted at the protein expression level, it is necessary to determine both the ApoE4 protein level and the total ApoE level.

A standard method of biomarker statistical analysis is to use univariate methods to compare biomarker levels in various groups and highlight those biomarkers whose concentrations significantly differ between groups.

The individual biomarkers selected for use in the method of the invention are analysed by Receiver Operator Characteristic (ROC) analysis. The ROC curve is a preferred method of assessing the accuracy of a diagnostic test as it addresses both the sensitivity (i.e. the number of true positives) and the specificity (i.e. the number of false positives) of the test. The biomarker(s) which give a high sensitivity and specificity (approximately 80% for both sensitivity and specificity are accepted values in the diagnostic field) form the basis of the logistic regression equation. The value of the measured protein concentration of the biomarker is inputted into the logistic regression equation to give a final value which can be used to aid the diagnosis of Alzheimer's disease.

To construct a ROC curve for multiple biomarkers, a logistic regression equation is derived for the biomarker combination of interest, by inputting measured protein concentration value of each of the biomarkers in a patient's sample into the equation.

Although a logistic regression equation is the preferred statistical method for the current invention, other conventional statistical methods can be used.

By way of example, considering two hypothetical analytes, A and B, the derived logistic regression equation for analyte A and analyte B is:

$$y = 3.2027 \times \log[A] - 0.9506 \times \log[B] + 0.1548$$

wherein [A] is the measured concentration of analyte A and [B] is the measured concentration of analyte B in a patient sample.

If y is above the cut-off value derived in the ROC curve, a diagnosis of Alzheimer's disease in a patient is supported. If y is below the cut-off value, the diagnosis of Alzheimer's disease is not supported.

The terms "control value" and "cut-off" are used interchangeably herein, and refer to a reference value against which the value obtained for the patient sample according to the method of the invention is compared in order to aid the diagnosis of Alzheimer's disease.

In order to obtain the control value, the expression level of the platelet proteins listed in step (i) of the method of the invention is determined from samples of a population of healthy individuals. The statistical tools of ROC curve analysis and linear regression are then applied to the results in order to obtain a single cut-off value.

It will be appreciated that the cut-off value will vary according to the size of the control population. Biological variation within the control population is reduced by increasing the size of the population. Therefore it is preferable if the control value is derived from a control population comprising at least 30 healthy individuals, preferably at least 50 healthy individuals and more preferably at least 100 healthy individuals.

A further embodiment of the method of the invention provides four different models for the diagnosis of Alzheimer's disease; these are summarised in Table 2. Model 1 comprises a single algorithm. Models 2, 3 and 4 each comprise two algorithms, which are selected depending upon the presence or absence of the ApoE4 genotype. The decision process for selecting the most appropriate algorithm for a given patient sample is illustrated in FIG. 1.

Model 1

Model 1 is based upon Algorithm A, which is independent of the presence of ApoE4 (i.e., this algorithm can be applied regardless of whether a patient has 0, 1 or 2 alleles of ApoE4). The results of the measurements of the assays marked with "X" are added together.

For each of the four models described herein, weighting factors can be applied to the expression values of each of the biomarkers, and these may differ for different biomarkers and depending upon whether the assay is being conducted using a biochip or 2D DIGE.

In its simplest form, using a weighting factor of 1 for all biomarkers, the result for a test subject would be determined using Model 1 by applying the following calculation:

1×standardised abundance(Mao-B)+1×standardised abundance(total tropomyosin)+1×standardised abundance(coagulation factor XIIIa)+1×standardised abundance(wtGSTO-1)+1×standardised abundance(ApoE4).

The result is then compared to the control value. A result higher than the control is indicative of Alzheimer's disease in the patient.

Model 2

Model 2 uses two different algorithms that take account of the over-representation of wtGSTO-1 in non-ApoE4 Alzheimer's disease patients. The use of the respective algorithm depends on the presence or absence of ApoE4 in the patient, thereby accounting for the over-representation of wt GSTO-1 in non-ApoE4 patients. If the ApoE4 allele is absent from the patient sample, Algorithm A is used. Otherwise, Algorithm B is used. The result is obtained by applying a weight factor to the standardised abundance of each biomarker, as explained above for Model 1.

Model 3

Model 3 also uses two different algorithms. Similarly to Model 2, if the ApoE4 allele is absent from the patient's genome then Algorithm A is applied. If the patient carries 1 or 2 ApoE4 alleles then Algorithm C is applied. The result is obtained by applying a weight factor to the standardised abundance of each biomarker, as explained above for Model 1.

Model 4

Model 4 is similar to Models 2 and 3, in that different algorithms (i.e. D or E) are used depending upon the presence of absence of ApoE4 in the patient's genome. However, Model 4 includes an additional biomarker, WD-repeat protein 1.

The resulting value calculated using the algorithms of Models 1, 2, 3 or 4 is compared to a pre-determined control value in order to aid the diagnosis of disease. An explanation of how control values may be determined is provided in Example 1.

respectively is added to the total standardised abundance value for all of the platelet proteins that are included in a given algorithm. The resulting value is then compared to the control in order for a diagnosis to be made. Alternatively, if the patient has no alleles of ApoE4 then no additional weighting factor is added to the total standardised abundance value.

According to the present invention, the diagnosis of Alzheimer's disease can be aided by comparing the total expression level of each of the biomarkers in the isolated platelet sample to a control value. Diagnosis of disease may be achieved in combination with other factors such as clinical observations and patient history, and by reference to previous assay results from the patient.

However, since platelets are differently concentrated in the blood, the concentration of platelet proteins also varies. The coefficient of variation for platelet concentration in platelet-rich plasma and gel-filtered platelets is 38% and 32% respectively, and the correlation of the of the platelet count to the platelet concentration is poor (K=0.58 for an analytical normalisation of platelet biomarkers by the platelet count). This makes the concentration of platelet proteins in a blood sample an unreliable indicator for determination of pathological changes in the brain and additional steps to normalise platelet protein concentrations are required.

Therefore, the present invention utilises internal extraction standards to enable the accurate quantification of expression of platelet proteins in terms of "standardised abundance".

In a preferred embodiment, internal extraction standard is derived from the human platelet proteome and is present in a patient sample, or control sample, of platelet lysate.

As used herein, the term 'low biological variation' refers to cell extract proteins with a CV value of less that 0.18.

As used herein, the term 'normalise natural biological variation' refers to the use of a reference value corresponding to the concentration of a protein which varies negligibly between samples, against which the concentration of proteins with higher natural variation between samples can be accurately determined.

Candidate proteins for internal extraction standards were identified by analysing the biological variation of 908 different proteins within the platelet proteome of 110 individuals, using bioinformatic analysis, mass spectrometry and 2D

TABLE 2

| | | | Algorithm contains: | | | | | |
|---|---|---|---|---|---|---|---|---|
| | | | Standardised abundance of (2D-DIGE) | | | | | |
| Model | Algorithm | Applied to patients | Mao-B | Total tropomyosin | Coagulation Factor XIIIa | WD-repeat protein 1 | wt GSTO-1 | Mutant GSTO-1 | ApoE4 |
| 1 | A | all | X | X | X | — | X | — | X |
| 2 | A | ApoE4-neg. | X | X | X | — | X | — | X |
| | B | ApoE4-pos. | X | X | X | — | — | — | X |
| 3 | A | ApoE4-neg. | X | X | X | — | X | — | X |
| | C | ApoE4-pos. | X | X | X | — | — | X | X |
| 4 | D | ApoE4-neg. | X | X | X | X | X | — | X |
| | E | ApoE4-pos. | X | X | X | X | — | X | X |

X The respective assay is included in the algorithm
— The respective assay is not included in the algorithm Each of the algorithms described in the above Models 1-4 can also comprise a weighting factor based on the number of alleles of ApoE4 present in the patient's genome. If the patient carries one or two alleles of ApoE4, a value of +1 or +2 respectively is added to the total standardised abundance value for all of the platelet proteins that are included in a given algorithm.

PAGE. Table 3 lists candidates with a low biological variation identified on gels with the pH range of 4-7. Table 4 lists candidates with a low biological variation identified on gels with the pH range of 6-9.

TABLE 3

| Protein Name | Swissprot Accession No. | CV-all |
| --- | --- | --- |
| 14-3-3 gamma | P61981 | 0.084 |
| Peroxiredoxin-6 | P30041 | 0.086 |
| Growth factor receptor-bound protein 2 | P62993 | 0.088 |
| F-actin capping protein beta subunit (Cap Z beta) | P47756 | 0.088 |
| Serine/threonine-protein phosphatase PP1-alpha catalytic subunit | P62136 | 0.089 |
| Myosin light protein 6 | P60660 | 0.092 |
| Microtubule-associated protein RP/EB family member 2 | Q15555 | 0.092 |
| Rab GDP dissociation inhibitor beta (Rab GDI beta) | P50395 | 0.093 |
| Programmed cell death 6-interacting protein (PDCD6-interacting protein) | Q8WUM4 | 0.095 |
| Alpha-soluble NSF attachment protein (SNAP-alpha) | P54920 | 0.095 |
| Guanine nucleotide-binding protein G(I)/G(S)/G(T) subunit beta 1 | P62873 | 0.095 |
| 14-3-3 protein theta | P27348 | 0.099 |
| 14-3-3 protein zeta/delta | P63104 | 0.099 |
| GRP75 Mortalin | P38646 | 0.104 |
| Protein disulfide-isomerase A6 | Q15084 | 0.112 |
| Integrin α-IIb | P08514 | 0.143 |
| Nucl. Assembly prot 1 | P55209 | 0.177 |

TABLE 4

| Protein Name | SwissProt Accession No. | CV-all |
| --- | --- | --- |
| Profilin-1 | P07737 | 0.074 |
| Cyclophilin A | P62937 | 0.082 |
| Cyclophilin A | P62937 | 0.092 |
| Triosephospahate-Isomerase | P60174 | 0.103 |
| Mitogen-activated protein kinase 1 (ERK2) | P28482 | 0.103 |
| Voltage-dependent anion-selective channel protein 3 | Q9Y277 | 0.112 |
| Fructose-bisphosphate aldolase A | P04075 | 0.115 |
| Calponin-2 (Calponin H2; smooth muscle) (Neutral calponin) | Q99439 | 0.115 |
| Tyrosyl-tRNA synthetase; ctyoplasmic | P54577 | 0.120 |
| Dual specificity protein phosphatase 3 | P51452 | 0.121 |
| Actin-related protein 2/3 complex subunit 2 | O15144 | 0.125 |
| Isocitrate Dehydrogenase | P48735 | 0.128 |
| Protein-L-isoaspartate (D-aspartate) O-methyltransferase | P22061 | 0.128 |
| Glyceraldehyde-3-phosphate dehydrogenase | P04406 | 0.129 |
| Proteasome subunit alpha type 2 | P25787 | 0.129 |
| Proteasome subunit alpha type 4 | P25789 | 0.137 |
| Proteasome subunit alpha type 7 | O14818 | 0.147 |
| Glyceraldehyde-3-phosphate dehydrogenase | P04406 | 0.155 |

Therefore, a second aspect of the present invention relates to the use of one or more proteins listed in Tables 3 or 4 to normalise biological variation in the expression level of one or more platelet proteins included in the method of the first aspect of the present invention.

Suitable proteins may be identified according to their SwissProt Primary Accession Numbers. The SwissProt accession number identifies the mRNA product that codes for each protein.

The UniProtKB/SwissProt protein knowledgebase is an annotated protein sequence database established by the merger of the SwissProt and UniProt knowledgebase protein databases. It is maintained collaboratively by the Swiss Institute for Boinformatics (SIB), the European Bioinformatics Institute (EBI) and the National Biomedical research Foundation. The UniProtKB/SwissProt release referred to herein is v55.2, of 8 Apr. 2008, and can be accessed at http://expasy.org/sprot.

All proteins deriving from this mRNA are within the scope of the invention, i.e. all variants and post-translational modifications.

In a preferred embodiment of the invention, the internal extraction standard protein is 14-3-3 protein gamma.

In a third aspect of the present invention provides a biochip which comprises a solid support comprising discrete test regions in which at least platelet proteins selected from monoamine oxidase-B, coagulation factor XIIIa, tropomyosin (α and β), WD-repeat protein 1 and ApoE4 are immobilised. In a preferred embodiment, the solid support further comprises immobilised ligands for one or more of the proteins identified in Table 3 or Table 4. Preferably, the solid support further comprises one or more ligands of wild-type GSTO-1, mutant GSTO-1 and apolipoprotein E.

Use of the biochip of the invention enables multi-analyte screening of the patient sample in a rapid, accurate and easy to use format. The multi-analyte approach has benefits beyond time and cost savings, which are vital in the drive towards increasing efficiencies and improved clinical performance. Traditional diagnosis takes the form of single analyte assays, even though several are usually required, thus increasing sample volumes, possibly requiring multiple patient attendance and increasing the time before diagnosis. The multi-analyte assay reduces patient discomfort, as all the assays are conducted using a single patient sample, negating the need for multiple patient sampling.

As used herein, the term ligand refers to a molecule that binds to a target. The ligands of the biochip of the invention may be antibodies, antigens or nucleic acids.

As can be understood from Table 2, the application of algorithm A requires the biochip to comprise ligands for monoamine oxidase-B, coagulation factor XIIIa, α-tropomyosin, β-tropomyosin, apolipoprotein E4, apolipoprotein E and wild-type (wt) GSTO-1. The application of algorithm B requires the biochip to comprise ligands for monoamine oxidase-B, coagulation factor XIIIa, α-tropomyosin, β-tropomyosin, apolipoprotein E4, apolipoprotein E only. The application of Algorithm C requires the biochip to comprise ligands for monoamine oxidase-B, coagulation factor XIIIa, α-tropomyosin, β-tropomyosin, apolipoprotein E4, apolipoprotein E and mutant (mt) GSTO-1. The application of algorithms D and E require the biochip to comprise ligands for monoamine oxidase-B, coagulation factor XIIIa, α-tropomyosin, β-tropomyosin, WD-repeat protein 1, apolipoprotein E4, apolipoprotein E and wt-GSTO-1 (algorithm D only) and mt-GSTO-1 (algorithm E only).

If only genotyping data for (wt) GSTO-1 and (mt) GSTO-1 are included in the models then the assays for wild-type (wt) GSTO-1 and mutant (mt) GSTO-1 are interchangeable. If genotyping via the protein expression level is possible the protein assays for (wt) GSTO-1 and (mt) GSTO-1 are also interchangeable. However, the use of genotyping data only will result in decreased accuracy of diagnosis, since the models perform better when the respective protein concentrations are used.

The expression of the specific platelet proteins in a patient sample according to the invention is quantified in terms of standardised abundance, preferably using a biochip array system. The biochip of the invention is contacted with a patient platelet cell lysate sample and then washing the surface, such that proteins present in the sample are identified according to the interactions formed with ligands immobilised on the biochip surface. Ligand-protein interactions produce chemiluminescence signals that can be rapidly detected and analysed using an imaging system, such as a charge-coupled device (CCD) super cooled camera, to simultaneously quantify the individual analytes. Sample addition to the biochip and the subsequent wash, incubation and signal reagent steps can be either entirely automated or by manual application. The results of the platelet protein expression measurement undergo two consecutive normalisation procedures. The first involves a procedure for the correction of technical variation of the signals that are obtained with the biochip array system, such as background correction, reference spot and correction spot validation.

Comparisons of signals of the unknown sample with calibration curves give the protein concentrations of the unknown sample. The platelet concentration in whole blood and in the isolated samples varies between individuals and hence affects the AD biomarker protein concentration in the samples. Therefore, a second standardisation procedure, the calculation of the standardised abundance of the Alzheimer's disease biomarkers, is necessary. One or more internal extraction standard proteins (selected from Tables 3 and 4) is measured in parallel with the Alzheimer's disease biomarkers. The standardised abundance value corresponds to the ratio between the expression levels of the Alzheimer's disease biomarker and the internal extraction standard, or the sum of multiple internal extraction standards.

Alternatively, expression levels can be determined using a 2D DIGE analysis and calculating the standardised abundance of the respective spots on the gel using software such as the DeCyder software 6.5 (GE Healthcare).

In the 2D DIGE system, there are also two consecutive procedures used to obtain the standardised abundance of a protein. The first procedure (the normalization) involves the calculation of a normalisation factor by calculating a data histogram from spot ratios between the primary and the secondary gel images. A normal distribution curve is fitted to the histogram and the resulting centre of the model curve is the normalisation factor. The spot volumes in the primary spot map are then normalised using the normalisation factor $$C': V1i' = V1i \times 10 C(ii)$$

wherein: V1i' is the normalised volume of spot i in the primary gel image; and V1i is the volume of spot i in the primary gel image The second procedure involves the use of an internal standard that usually is a pool of all samples tested in the study and is present on each 2-dimensional DIGE gel. The standardized volume ratio for each standard image from the different gels is set to the value 1.0. The expression ratio for each sample spot is then related to its corresponding standard spot in the same gel, thus making it possible to compare ratios between matched protein spots in the different gels.

The resulting standardised abundance value is the ratio between the normalised protein spot volume and the normalised internal standard spot volume described in terms of fold change.

The above-mentioned calculations can be modified by the use of $Log_{10}$ of the standardised values in order to aid scaling in graphical representations and statistical analyses.

The following non-limiting examples illustrate aspects of the invention.

Example 1

Analysis of Single Biomarker Assays and Assays Comprising Three, Four and Five Biomarkers for the Diagnosis of Alzheimer's Disease Samples were collected in two phases and divided into a discovery set and validation set. The standard abundance of each platelet protein was measured using 2D-DIGE and ROC curves were generated in order to obtain optimal cut-off, actual cut-off, sensitivity and specificity values for each biomarker. The results for each of these single protein assays are shown in Table 5.

TABLE 5

| Single Assay | Sample set | ROC curve AUC | 95% CI | Significance | Optimal cut-off | Actual cut-off | Sensitivity (%) | Specificity (%) |
|---|---|---|---|---|---|---|---|---|
| MAO-B | Discovery | 0.847 | 0.714-0.980 | <0.001 | 1.072 | 1.072 | 89 | 80 |
|  | Validation | 0.826 | 0.689-0.964 | <0.001 | 1.048 | 1.072 | 75.1 | 80 |
| Total tropomyosin | Discovery | 0.797 | 0.655-0.940 | 0.002 | 1.802 | 1.802 | 83.3 | 65 |
|  | Validation | 0.704 | 0.539-0.869 | 0.027 | 1.748 | 1.802 | 56.5 | 76.2 |
| Coagulation Factor XIIIa | Discovery | 0.761 | 0.601-0.921 | 0.006 | 1.036 | 1.036 | 78 | 65 |
|  | Validation | 0.717 | 0.551-0.883 | 0.019 | 0.929 | 1.036 | 47.4 | 79 |
| ApoE4 | Discovery | 0.797 | 0.647-0.947 | 0.002 | 0.5 | 0.5 | 67 | 90 |
|  | Validation | 0.744 | 0.585-0.904 | 0.008 | 0.5 | 0.5 | 58 | 91 |
| wt GSTO-1 | Discovery | 0.574 | 0.387-0.760 | 0.438 | 0.875 | 0.875 | 78 | 50 |
|  | Validation | 0.61 | 0.432-0.788 | 0.233 | 0.805 | 0.875 | 47.4 | 57.1 |
| mt GSTO-1 | Discovery | 0.368 | 0.189-0.548 | 0.165 | N/A | N/A | N/A | N/A |
|  | Validation | 0.486 | 0.300-0.673 | 0.882 | N/A | N/A | N/A | N/A |

Algorithms were developed for assaying combinations of three and four biomarkers simultaneously, in order to obtain cut-off (control) values, for use as reference values in the diagnosis of Alzheimer's disease. These algorithms are summarised in Table 6.

TABLE 6

| | Algorithm contains | | | | |
|---|---|---|---|---|---|
| | Standardised Abundances of (2D-DIGE) | | | | Genotyping: |
| Combination of Markers | Mao-B | Total Tropo-myosin | Coagulation factor XIIIa | wt GSTO1 | Alleles of APOE4 |
| 3-marker comb. 1 | X | — | — | X | X |
| 3-marker comb. 2 | X | X | — | — | X |
| 3-marker comb. 3 | X | — | X | — | X |
| 3-marker comb. 4 | X | X | — | X | — |
| 3-marker comb. 5 | X | — | X | X | — |
| 3-marker comb. 6 | X | X | X | — | — |
| 3-marker comb. 7 | — | X | — | X | X |
| 3-marker comb. 8 | — | — | X | X | X |
| 3-marker comb. 9 | — | X | X | — | X |
| 3-marker comb. 10 | — | X | X | X | — |
| 4-marker comb. 1 | X | X | — | X | X |
| 4-marker comb. 2 | X | — | X | X | X |

TABLE 6-continued

| | Algorithm contains | | | | |
|---|---|---|---|---|---|
| | Standardised Abundances of (2D-DIGE) | | | | Geno-typing: Alleles of APOE4 |
| Combination of Markers | Mao-B | Total Tropo-myosin | Coagulation factor XIIIa | wt GSTO1 | |
| 4-marker comb. 3 | X | X | X | — | X |
| 4-marker comb. 4 | X | X | X | X | — |
| 4-marker comb. 5 | — | X | X | X | X |

A theoretical threshold was set above which all values indicate a positive AD diagnosis. The values calculated for each algorithm were compared with the theoretical threshold and results higher than the threshold corresponded to a positive diagnosis for Alzheimer's disease. These diagnoses were then compared to the actual diagnosis from two test groups (AD group and control group). From this comparison false positives and the false negatives were determined and specificity and sensitivity values were calculated. Each point in the ROC curve corresponds to a threshold (control value) with specific specificity and sensitivity.

To get the whole ROC curve, the value of the theoretical threshold was continually increased and for each threshold the specificity and sensitivity was determined. The point of the ROC curve closest to the upper left corner of the graph corresponds to the optimal cutoff, i.e. the highest sensitivity and specificity values. The distance of the each point from the upper left corner (0,1) in the ROC curve was calculated using the formula: Distance=$\sqrt{(1-\text{sensitivity})^2+(1-\text{specificity})^2}$ The point with the lowest distance value corresponds to the control value with the best specificity and sensitivity. The results derived from the ROC curves are shown in Table 7.

Finally, the algorithms of Models 1-4 were devised. These take into consideration the expression of the seven biomarkers of the invention (see Table 2).

ROC curves were generated for these biomarker combinations and control values were calculated from the resulting scatter plots (see FIGS. 2 to 4). In addition, Models 2 and 3 take into consideration the finding that wild-type GSTO-1 is overrepresented in Alzheimer's disease patients who do not carry any APOE4 allele, whereas wtGSTO-1 is under-represented in APOE4-positive Alzheimer's disease patients.

The results for Models 1-3 are shown in Table 8. When assessing the data, high values for area under the ROC curve (AUC), and high specificity and sensitivity values are desirable, as they indicate the most accurate assays. The values for "actual cut-off" are highlighted; these are the control values used in the method of the invention for the diagnosis of Alzheimer's disease.

As can be seen from the results in Table 8, Model 3 has the highest AUC values (0.949), and is the most accurate assay. It is likely that Model 3 gives better results than Model 1 because it takes into account the differences between ApoE4-positive and ApoE4-negative AD patients regarding the GSTO-1 genotype.

In Model 3, algorithm A is only used for ApoE4-negative test subjects. To diagnose ApoE4-positive subjects, a second algorithm that fits better to ApoE4-positive test subjects is required. Therefore, there are two algorithms (A and C) in Model 3 and each is used only for a particular group of test subjects (ApoE4-negative test persons or ApoE4-positive test persons), thereby increasing the accuracy of AD diagnosis.

Figure 5:
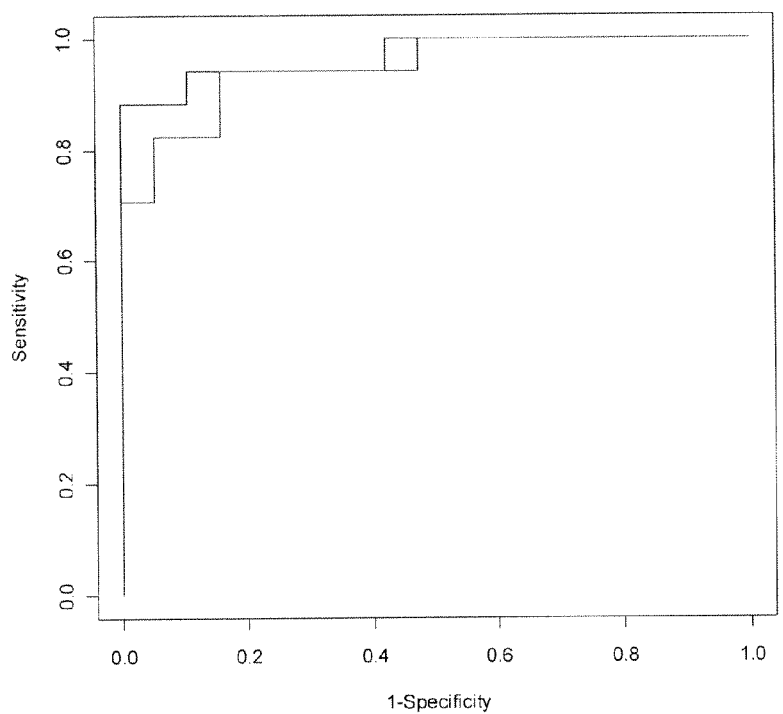
FIG. 5 shows the ROC curve for Model 4.

Model 4 comprises algorithms D and E (ApoE4-negative and ApoE4-positive respectively). These algorithms differ from A-C in that they include the platelet protein WD-repeat protein 1. The weighting factors for each protein, derived using a cut-off value of 8.1, are shown in Table 9. The ROC curve (AUC) is shown as FIG. 5.

TABLE 7

| Algorithm | Sample Set | ROC Curve AUC | 95% CI | Significance | Optimal Cutoff | Actual Cutoff | Sensitivity [%] | Specificity [%] |
|---|---|---|---|---|---|---|---|---|
| 3-marker comb. 1 | discovery | 0.853 | 0.733-0.973 | <0.001 | 2.669 | 2.669 | 88.9 | 75.0 |
| | validation | 0.882 | 0.755-1.000 | <0.001 | 2.503 | 2.669 | 73.7 | 85.7 |
| 3-marker comb. 2 | discovery | 0.911 | 0.803-1.000 | <0.001 | 3.449 | 3.449 | 83.3 | 90.0 |
| | validation | 0.895 | 0.775-1.000 | <0.001 | 3.128 | 3.449 | 79.0 | 90.5 |
| 3-marker comb. 3 | discovery | 0.897 | 0.794-1.000 | <0.001 | 2.192 | 2.192 | 88.9 | 80.0 |
| | validation | 0.88 | 0.774-0.989 | <0.001 | 2.090 | 2.192 | 84.2 | 85.7 |
| 3-marker comb. 4 | discovery | 0.814 | 0.680-0.948 | 0.001 | 4.285 | 4.285 | 77.8 | 75.0 |
| | validation | 0.764 | 0.618-0.911 | 0.004 | 3.569 | 4.285 | 36.8 | 85.7 |
| 3-marker comb. 5 | discovery | 0.731 | 0.568-0.893 | 0.015 | 3.349 | 3.349 | 72.2 | 65.0 |
| | validation | 0.794 | 0.652-0.937 | 0.001 | 2.710 | 3.349 | 36.8 | 85.7 |
| 3-marker comb. 6 | discovery | 0.875 | 0.761-0.989 | <0.001 | 4.011 | 4.011 | 88.9 | 75.0 |
| | validation | 0.83 | 0.696-0.964 | <0.001 | 3.675 | 4.011 | 52.6 | 95.2 |
| 3-marker comb. 7 | discovery | 0.903 | 0.804-1.000 | <0.001 | 3.719 | 3.719 | 83.3 | 90.0 |
| | validation | 0.832 | 0.699-0.965 | <0.001 | 3.112 | 3.719 | 47.4 | 85.7 |
| 3-marker comb. 8 | discovery | 0.856 | 0.740-0.972 | <0.001 | 2.297 | 2.297 | 88.9 | 70.0 |
| | validation | 0.815 | 0.672-0.957 | 0.001 | 1.969 | 2.297 | 73.7 | 71.4 |
| 3-marker comb. 9 | discovery | 0.906 | 0.708-1.000 | <0.001 | 3.547 | 3.547 | 83.3 | 100.0 |
| | validation | 0.857 | 0.734-0.981 | <0.001 | 3.060 | 3.547 | 49.4 | 90.5 |
| 3-marker comb. 10 | discovery | 0.814 | 0.680-0.948 | 0.001 | 4.076 | 4.076 | 77.8 | 70.0 |
| | validation | 0.727 | 0.570-0.884 | 0.014 | 3.543 | 4.076 | 47.4 | 76.2 |
| 4-marker comb. 1 | discovery | 0.908 | 0.819-0.998 | <0.001 | 5.137 | 5.137 | 77.8 | 90.0 |
| | validation | 0.885 | 0.771-0.998 | <0.001 | 4.117 | 5.137 | 94.7 | 81.0 |
| 4-marker comb. 2 | discovery | 0.864 | 0.752-0.976 | <0.001 | 3.454 | 3.454 | 93.3 | 70.0 |
| | validation | 0.872 | 0.748-0.997 | <0.001 | 2.931 | 3.454 | 81.3 | 81.0 |
| 4-marker comb. 3 | discovery | 0.919 | 0.821-1.000# | <0.001 | 4.559 | 4.559 | 83.3 | 95.0 |
| | validation | 0.887 | 0.771-1.000 | <0.001 | 4.040 | 4.559 | 64.8 | 90.5 |
| 4-marker comb. 4 | discovery | 0.853 | 0.734-0.971 | <0.001 | 5.213 | 5.213 | 83.3 | 70.0 |
| | validation | 0.805 | 0.665-0.944 | <0.001 | 4.507 | 5.213 | 57.9 | 85.7 |
| 4-marker comb. 5 | discovery | 0.922 | 0.826-1.000 | <0.001 | 5.070 | 5.070 | 77.8 | 100.0 |
| | validation | 0.847 | 0.720-0.974 | <0.001 | 3.787 | 5.070 | 35.3 | 90.5 |

TABLE 8

| Single Assay or Model | Sample set | ROC curve AUC | 95% CI | Significance | Optimal Cutoff | Actual Cutoff | Sensitivity [%] | Specificity [%] |
|---|---|---|---|---|---|---|---|---|
| Moa-B | discovery | 0.847 | 0.714-0.980 | <0.001 | 1.072 | 1.072 | 89.0 | 80.0 |
|  | validation | 0.826 | 0.689-0.964 | <0.001 | 0.48 | 1.072 | 75.1 | 80.0 |
| total Tropomyosin | discovery | 0.797 | 0.655-0.940 | 0.002 | 1.802 | 1.802 | 83.3 | 65.0 |
|  | validation | 0.704 | 0.539-0.869 | 0.027 | 1.748 | 1.802 | 56.5 | 76.2 |
| Coagulation factor XIIIa | discovery | 0.761 | 0.601-0.921 | 0.006 | 1.036 | 1.036 | 78.0 | 65.0 |
|  | validation | 0.717 | 0.551-0.883 | 0.019 | 0.929 | 1.036 | 47.4 | 79.0 |
| APOE4 | discovery | 0.797 | 0.647-0.947 | 0.002 | 0.500 | 0.500 | 67.0 | 90.0 |
|  | validation | 0.744 | 0.585-0.904 | 0.008 | 0.500 | 0.500 | 58.0 | 91.0 |
| wt GSTO-1 | discovery | 0.574 | 0.387-0.760 | 0.438 | 0.875 | 0.875 | 78.0 | 50.0 |
|  | validation | 0.610 | 0.432-0.788 | 0.233 | 0.805 | 0.875 | 47.4 | 57.1 |
| mutant GSTO-1 | discovery | 0.368 | 0.189-0.548 | 0.165 | N/A | N/A | N/A | N/A |
|  | validation | 0.486 | 0.300-0.673 | 0.882 | N/A | N/A | N/A | N/A |
| mutant GSTO-1 (mirrored) | discovery | 0.632 | 0.452-0.812 | 0.165 | 1.29* | 1.29* | 72.2 | 50.0 |
|  | validation | 0.514 | 0.328-0.700 | 0.882 | 0.675 | 1.29* | 47.4 | 57.1 |
| 3-marker combo. 1 | discovery | 0.853 | 0.733-0.973 | <0.001 | 2.669 | 2.669 | 88.9 | 75.0 |
|  | validation | 0.882 | 755-1.000 | <0.001 | 2.503 | 2.669 | 73.7 | 85.7 |
| 3-marker combo. 2 | discovery | 0.911 | 0.803-1.000 | <0.001 | 3.449 | 3.449 | 83.3 | 90.0 |
|  | validation | 0.895 | 0.775-1.000 | <0.001 | 3.128 | 3.449 | 79.0 | 90.5 |
| 3-marker combo. 3 | discovery | 0.897 | 0.794-1.000 | <0.001 | 2.192 | 2.192 | 88.9 | 80.0 |
|  | validation | 0.88 | 0.774-0.989 | <0.001 | 2.090 | 2.192 | 84.2 | 85.7 |
| 3-marker combo. 4 | discovery | 0.814 | 0.680-0.948 | 0.001 | 4.285 | 4.285 | 77.8 | 75.0 |
|  | validation | 0.764 | 0.618-0.911 | 0.004 | 3.569 | 4.285 | 36.8 | 85.7 |
| 3-marker combo. 5 | discovery | 0.731 | 0.568-0.893 | 0.015 | 3.349 | 3.349 | 72.2 | 65.0 |
|  | validation | 0.794 | 0.652-0.937 | 0.001 | 2.710 | 3.349 | 36.8 | 85.7 |
| 3-marker combo. 6 | discovery | 0.875 | 0.761-0.989 | <0.001 | 4.011 | 4.011 | 88.9 | 75.0 |
|  | validation | 0.83 | 0.696-0.964 | <0.001 | 3.675 | 4.011 | 52.6 | 95.2 |
| 3-marker combo. 7 | discovery | 0.903 | 0.804-1.000 | <0.001 | 3.719 | 3.719 | 83.3 | 90.0 |
|  | validation | 0.832 | 0.699-0.956 | <0.001 | 3.112 | 3.719 | 47.4 | 85.7 |
| 3-marker combo. 8 | discovery | 0.856 | 0.740-0972 | <0.001 | 2.297 | 2.297 | 88.9 | 70.0 |
|  | validation | 0.815 | 0.672-0.957 | 0.001 | 1.969 | 2.297 | 73.7 | 71.4 |
| 3-marker combo. 9 | discovery | 0.906 | 0.708-1.000 | <0.001 | 3.547 | 3.547 | 83.3 | 100.0 |
|  | validation | 0.857 | 0.734-0.981 | <0.001 | 3.060 | 3.547 | 49.4 | 90.5 |
| 3-marker combo. 10 | discovery | 0.814 | 0.680-0.948 | 0.001 | 4.076 | 4.076 | 77.8 | 70.0 |
|  | validation | 0.727 | 0.570-0.884 | 0.014 | 3.543 | 4.076 | 47.4 | 76.2 |
| 4-marker combo. 1 | discovery | 0.908 | 0.819-0.998 | <0.001 | 5.13 | 5.137 | 77.8 | 90.0 |
|  | validation | 0.885 | 0.771-0.998 | <0.001 | 4.117 | 5.137 | 94.7 | 81.0 |
| 4-marker combo. 2 | discovery | 0.864 | 0.752-0.976 | <0.001 | 3.454 | 3.454 | 83.3 | 70.0 |
|  | validation | 0.872 | 0.748-0.997 | <0.001 | 2.931 | 3.454 | 81.3 | 81.0 |
| 4-marker combo. 3 | discovery | 0.919 | 0.821-1.000# | <0.001 | 4.559 | 4.559 | 83.3 | 95.0 |
|  | validation | 0.887 | 0.771-1.000 | <0.001 | 4.404 | 4.559 | 64.8 | 90.5 |
| 4-marker combo. 4 | discovery | 0.853 | 0.734-0.971 | <0.001 | 5.213 | 5.213 | 83.3 | 70.0 |
|  | validation | 0.805 | 0.665-0.944 | 0.001 | 4.507 | 5.213 | 57.9 | 85.7 |
| 4-marker combo. 5 | discovery | 0.922 | 0.826-1.000 | <0.001 | 5.070 | 5.070 | 77.8 | 100.0 |
|  | validation | 0.847 | 0.720-0.974 | <0.001 | 3.787 | 5.070 | 35.3 | 90.5 |
| Model 1 | discovery | 0.929 | 0.835-1.000 | <0.001 | 5.535 | 5.535 | 89.0 | 80.0 |
|  | validation | 0.875 | 0.757-0.992 | <0.001 | 4.760 | 5.535 | 65.8 | 90.5 |
| Model 2 | discovery | 0.907 | 0.815-0.999 | <0.001 | 5.405 | 5.405 | 83.3 | 80.0 |
|  | validation | 0.860 | 0.739-0.980 | <0.001 | 4.525 | 5.405 | 47.4 | 92.4 |
| Model 3 | discovery | 0.949 | 0.880-1.000 | <0.001 | 5.535 | 5.535 | 89.0 | 90.0 |
|  | validation | 0.925 | 0.831-1.000 | <0.001 | 5.270 | 5.535 | 83.0 | 95.2 |

TABLE 9

| Platelet Protein | Weighting Factor Estimate | Std. Error |
|---|---|---|
| APOE4 | −1.87244 | 3.93421 |
| Monoamine oxidase B | 2.46031 | 1.32922 |
| Coagulation factor XIIIa | 0.07643 | 0.06608 |
| WD repeat-containing protein 1 | −0.59423 | 0.34092 |
| Tropomyosin 2 spot 1 | 0.20222 | 0.31999 |
| Tropomyosin 1 | 0.71958 | 0.47836 |
| Tropomyosin 2 spot 2 | −0.81031 | 0.53019 |
| Wild type glutathione S transferase (APOE4-neg) | 0.36094 | 0.22099 |
| Mutant glutathione S transferase (APOE4-pos) | 1.69013 | 1013201 |

It should be noted however that these models and algorithms were optimised for 2D DIGE data, and are presented here to illustrate, rather then limit, the present invention. An optimised model and optimised algorithms for biochip data may differ from the 2D DIGE data. The principle of the model may remain the same but the weighting of the particular AD biomarkers very likely will differ.

Example 2

Figure 6:
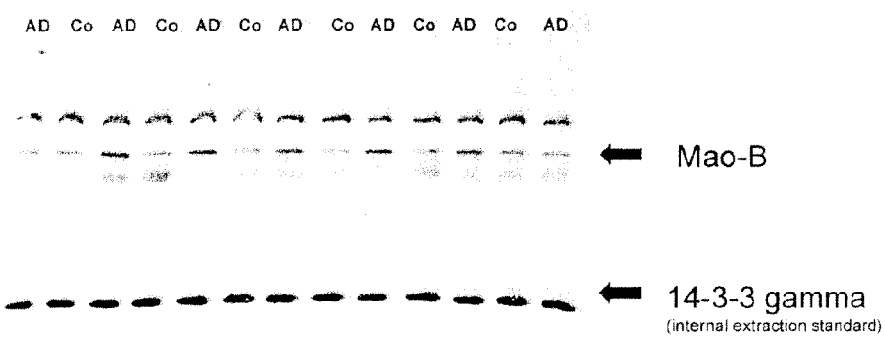
FIG. 6 is a 1D Western blot which shows the suitability of 14-3-3 gamma as an internal extraction standard.
Figure 7:
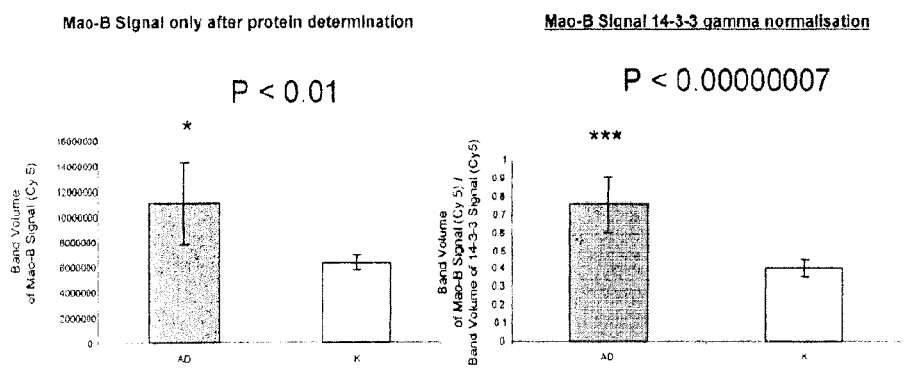
FIG. 7 is a comparison of increased Mao-B expression analysed after protein determination only (P<0.01) and following normalisation with the internal extraction protein 14-3-3 gamma (P<0.00000007)

Selection of 14-3-3 Gamma as an Internal Extraction Standard Protein 12.5 μg platelet protein from 24 Alzheimer's disease patients and 24 sex- and aged-matched controls was analysed in a 1D Western blot. The results are illustrated in FIG. 6 and show that the Mao-B signal is more intensive in platelet samples from Alzheimer's patients than control samples, whereas the intensity of the signal for 14-3-3 gamma is equal in all samples. As shown in FIG. 7, by measuring the Moa-B signal of 12.5 µg platelet protein without any normalisation only a low significant increase (P<0.01) can be detected in the Alzheimer's samples. After normalisation with 14-3-3 gamma however, the significance increases to P<0.00000007, which demonstrates that the precision with which a protein can be quantified in a sample increases enormously with the application of an internal extraction standard.

Figure 8:
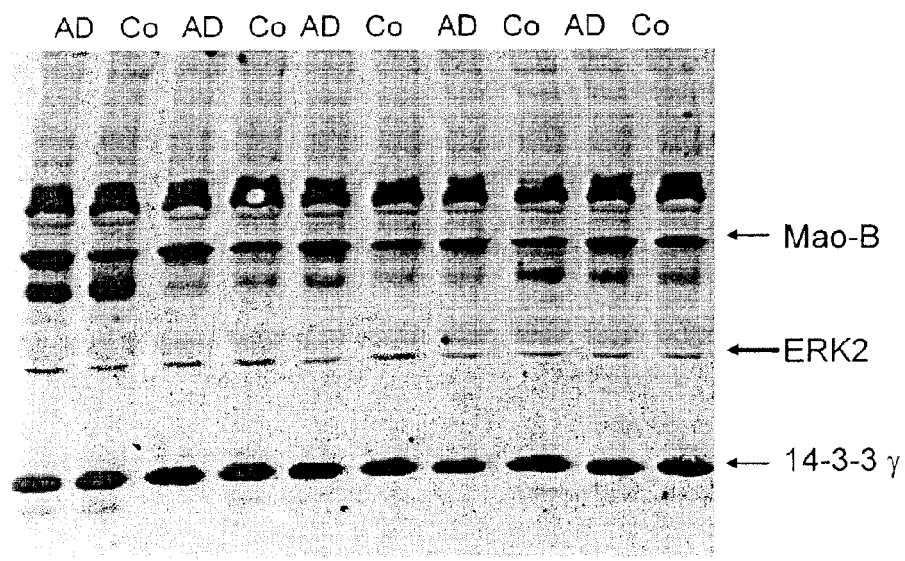
FIG. 8 is a representative Western blot for the application of ERK2 as an internal extraction standard.

FIG. 8 shows a representative Western blot for the application of ERK2 as an internal extraction standard. The signal for Mao-B expression in platelets of Alzheimer's patients is more intensive compared to the control samples, whereas the signals for 14-3-3 gamma and ERK2 is unchanged in all the platelet samples.

Example 3

Verification of Alzheimer's Disease Polymorphism in GSTO-1

Figure 9:
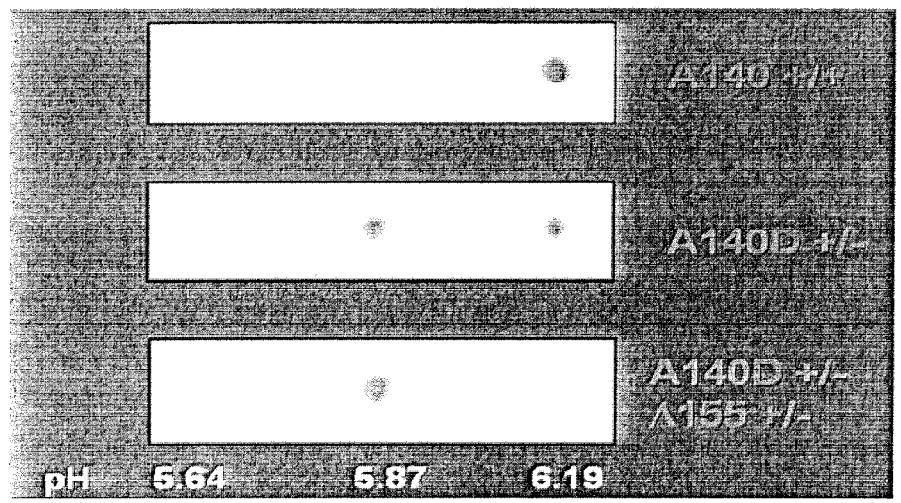
FIG. 9 shows three 2D Western blots of GSTO-1 isoforms.

2D gel electrophoresis analysis revealed three GSTO-1 isoforms with pI values of 6.19, 5.87 and 5.64 (FIG. 9). These isoforms show distinct expression patterns in the three groups: AD patients, PD patients and age- and sex-matched controls. Gel-filtered platelet samples of non-ApoE Alzheimer's patients revealed significant up-regulation of the GSTO-1 isoform with pI 6.19 (increased by 35%), whereas the GSTO-1 isoform with pI 5.87 is down-regulated by 60%.

The results in FIG. 9 represent two mis-sense polymorphisms in exon 4 of GSTO-1 (Ala140Asp and Glu155A). The GSTO-1 spot with pI 6.19 corresponds to WT. The spot with pI 5.87 represents an isoform where Ala140 is substituted by Asp (Ala140Asp). The spot with pI 5.64 may relate to a post-translational modification of unknown origin. Equal expression of the GSTO-1 spots with pI 6.19 and pI 5.87 correspond to a WT isoform and an isoform comprising the Ala140Asp substitution respectively. An exclusive spot at pI 5.87 represents a homozygous Asp/Asp GSTO-1 genotype at amino acid position 140. Alternatively, it may be observed in individuals carrying a deletion of Glu155Δ on one allele and an Ala140Asp GSTO-1 genotype on the other allele. Only the polypeptide carrying Asp 140 will be detected as the polypeptide carrying the Glu155Δ deletion might not be expressed or rapidly be degraded.

Example 4

Discrimination Between Alzheimer's Disease and Parkinson's Disease

The method of the present invention can be used to discriminate between patients suffering from Alzheimer's disease and those suffering from Parkinson's disease (PD), and Table 10 shows the comparison between AD samples and PD samples.

Figure 10:
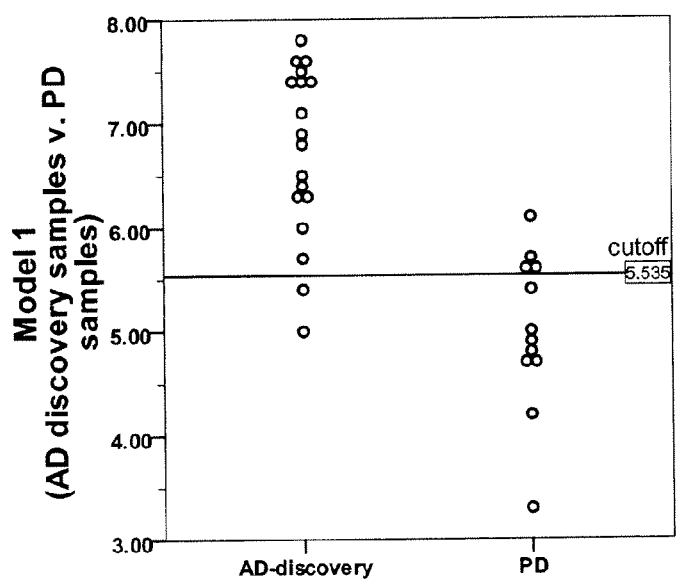
FIG. 10 shows a scatter plot for Alzheimer's and Parkinson's disease patient samples using Model 1.

FIG. 10 shows a scatter plot for a group of Alzheimer's disease patients (AD discovery group) and a group of Parkinson's disease patients. This result was obtained by applying the algorithm of Model 1 to platelet samples derived from a group of Parkinson's disease patients and a group of Alzheimer's disease patients, in accordance with the method of the invention. The calculated mean for the Alzheimer's disease patients in the discovery phase was 6.92±1.25 (SD) and 5.00±±0.74 (SD) for the Parkinson's disease patients. The cut-off was set at 5.535, which is the cut-off value determined for the Alzheimer's disease discovery set for Model 1 (see FIGS. 2a and 2b). As can be seen from the resulting scatter plot, there is a clear distinction between the results from the two patient groups.

Figure 11:
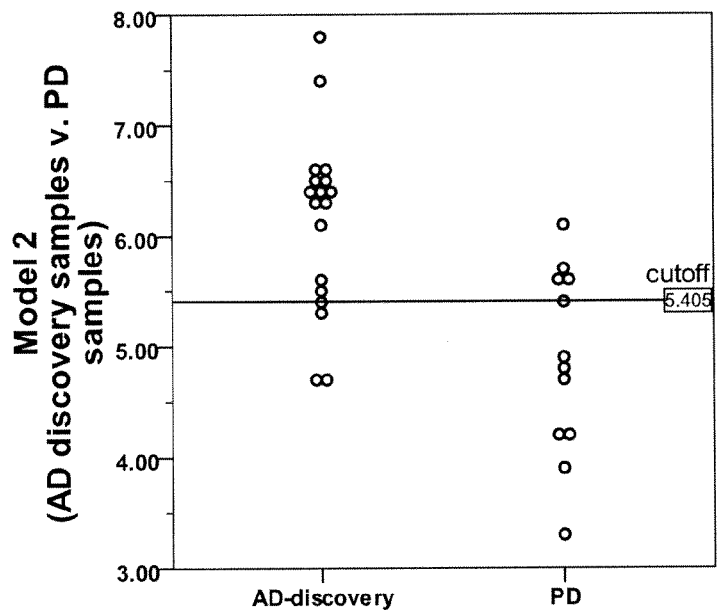
FIG. 11 shows a scatter plot for Alzheimer's and Parkinson's disease patient samples using Model 2.

Similarly, FIG. 11 shows a scatter plot for a group of Alzheimer's disease patients (AD discovery group) and a group of Parkinson's disease patients, which was obtained by applying Model 2 to platelet samples derived from the two patient groups. The calculated mean for the Alzheimer's disease patients in the discovery phase was 6.12±0.82 (SD) and 4.87±0.83 (SD) for the Parkinson's disease patients. The cut-off was set at 5.405, which is the cut-off value determined for the Alzheimer's disease discovery set for Model 2 (see FIGS. 3a and 3b). Again, there is a clear distinction between the distributions of the points on the scatter plot for each patient group.

Figure 12:
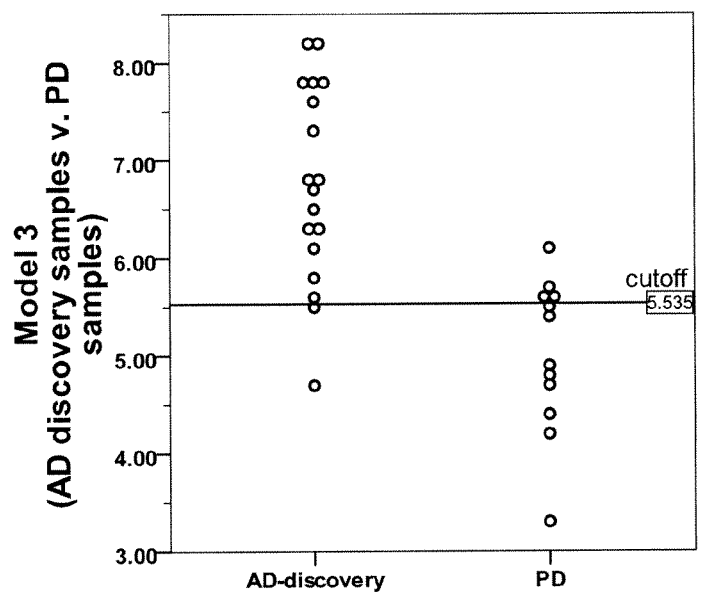
FIG. 12 shows a scatter plot for Alzheimer's and Parkinson's disease patient samples using Model 3.

FIG. 12 shows a scatter plot for a group of Alzheimer's disease patients (AD discovery group) and a group of Parkinson's disease patients, which was obtained by applying Model 3 to platelet samples derived from the two patient groups. The calculated mean for the Alzheimer's disease patients in the discovery phase was 6.28±0.93 (SD) and 5.01±0.77 (SD) for the Parkinson's disease patients. The cut-off was set at 5.535, which is the cut-off value determined for the Alzheimer's disease discovery set for Model 3 (see FIGS. 4a and 4b). This result shows that all three Models of the method of the invention can be applied in a diagnostic assay to discriminate between Alzheimer's disease and Parkinson's disease.

TABLE 10

| AD versus PD Single assays, combinations or Models | ROC curve AUC | 95% CI | Significance | Optimal Cut-off | Actual Cut-off | Sensitivity [%] | Specificity [%] |
|---|---|---|---|---|---|---|---|
| Mao-B | 0.981 | 0.944-1.00 | <0.001 | 0.998 | 1.072 | 89.0 | 100.0 |
| total Tropomyosin | 0.722 | 0.538-0.906 | 0.042 | 2.027 | 1.802 | 82.0 | 50.0 |
| Coagul. factor XIIIa | 0.769 | 0.575-0.962 | 0.014 | 1.007 | 1.036 | 75.2 | 83.3 |
| APOE4 | 0.773 | 0.605-0.941 | 0.013 | 0.500 | 0.5 | 66.7 | 83.3 |
| wtGSTO-1 | 0.519 | 0.278-0.759 | 0.866 | 0.870 | 0.875 | 76.3 | 50.0 |
| mutant GSTO-1 mirrored | 0.546 | 0.325-0.768 | 0.672 | 1.3249* | 1.29* | 41.7 | 72.2 |
| 3-marker comb. 1 | 0.894 | 0.776-1.000 | <0.001 | 2.665 | 2.669 | 88.3 | 75.0 |
| 3-marker comb. 2 | 0.903 | 0.783-1.000 | <0.001 | 3.430 | 3.449 | 83.0 | 100.0 |
| 3-marker comb. 3 | 0.894 | 0.768-1.000 | <0.001 | 2.080 | 2.192 | 87.7 | 75.0 |
| 3-marker comb. 4 | 0.787 | 0.618-0.956 | 0.009 | 4.284 | 4.285 | 77.7 | 66.7 |
| 3-marker comb. 5 | 0.764 | 0.583-0.945 | 0.016 | 3.314 | 3.349 | 72.2 | 66.7 |
| 3-marker comb. 6 | 0.903 | 0.787-1.000 | <0.001 | 4.105 | 4.011 | 88.9 | 82.4 |
| 3-marker comb. 7 | 0.852 | 0.714-0.990 | 0.001 | 3.750 | 3.720 | 83.3 | 77.9 |

TABLE 10-continued

| AD versus PD Single assays, combinations or Models | ROC curve AUC | 95% CI | Significance | Optimal Cut-off | Actual Cut-off | Sensitivity [%] | Specificity [%] |
|---|---|---|---|---|---|---|---|
| 3-marker comb. 8 | 0.787 | 0.625-0.949 | 0.009 | 2.880 | 2.297 | 85.3 | 66.7 |
| 3-marker comb. 9 | 0.880 | 0.714-1.000 | 0.001 | 3.421 | 3.547 | 79.4 | 100.0 |
| 3-marker comb. 10 | 0.711 | 0.523-0.898 | 0.054 | 4.880 | 5.070 | 39.6 | 91.7 |
| 4-marker comb. 1 | 0.912 | 0.775-1.000 | <0.001 | 4.803 | 5.137 | 74.5 | 91.7 |
| 4-marker comb. 2 | 0.880 | 0.760-1.000 | 0.001 | 3.750 | 3.454 | 82.6 | 75.0 |
| 4-marker comb. 3 | 0.931 | 0.821-1.000 | <0.001 | 4.241 | 4.559 | 81.4 | 100.0 |
| 4-marker comb. 4 | 0.801 | 0.644-0.958 | 0.006 | 4.893 | 5.213 | 78.8 | 58.3 |
| 4-marker comb. 5 | 0.875 | 0.749-1.00 | 0.001 | 5.031 | 5.070 | 73.0 | 91.7 |
| Model 1 | 0.940 | 0.862-1.00 | <0.001 | 5.623 | 5.535 | 88.9 | 70.7 |
| Model 2 | 0.843 | 0.704-0.981 | 0.002 | 5.869 | 5.405 | 83.3 | 66.7 |
| Model 3 | 0.917 | 0.815-1.000 | <0.001 | 5.764 | 5.535 | 86.9 | 66.7 |

The invention claimed is:

1. An ex vivo method for detecting platelet proteins, comprising
detecting at least four platelet proteins in a platelet sample from the patient selected from monoamine oxidase-B, coagulation factor XIIIa, total tropomyosin (α and β), WD-repeat protein 1 and apolipoprotein E4 (ApoE4), wherein said detecting comprises contacting a biochip array with the platelet sample, wherein the biochip array comprises a solid support having antibodies of the platelet proteins immobilized thereon.

2. The method according to claim 1, further comprising detecting either wild-type GSTO-1 or mutant GSTO-1.

3. The method according to claim 1, further comprising detecting the number of alleles of ApoE4 in the patient's genome.

4. The method according to claim 3, wherein there are no alleles of ApoE4 in the patient's genome and said method comprises detecting monoamine oxidase-B, coagulation factor XIIIa, total tropomyosin (α and β) and wild-type GSTO-1.

5. The method according to claim 4, further comprising detecting WD-repeat protein 1.

6. The method according to claim 3, wherein there are one or two alleles of ApoE4 in the patient's genome and said method comprises detecting monoamine oxidase-B, coagulation factor XIIIa and total tropomyosin (α and β) and ApoE4.

7. The method according to claim 6, further comprising detecting the level of expression of mutant GSTO-1.

8. The method according to claim 7, further comprising detecting the level of expression of WD-repeat protein 1.

9. A solid support comprising antibodies of at least four platelet proteins selected from monoamine oxidase-B, coagulation factor XIIIa, tropomyosin (α and β), WD-repeat protein 1 and ApoE4, immobilized thereon.

10. The solid support according to claim 9, further comprising antibodies of one or more of the proteins identified in Table 3 or Table 4, immobilized thereon.

11. The solid support according to claim 9, further comprising an antibody of wild-type GSTO-1 protein.

12. The solid support according to claim 9, further comprising an antibody of mutant GSTO-1 protein.

13. The solid support according to claim 9, further comprising an antibody of an apolipoprotein E protein.

* * * * *